(12) United States Patent
Edwards et al.

(10) Patent No.: US 10,898,347 B2
(45) Date of Patent: Jan. 26, 2021

(54) SURGICAL INSTRUMENT AND METHOD OF USE

(71) Applicant: DePuy Ireland Unlimited Company, County Cork (IE)

(72) Inventors: Jon M. Edwards, Warsaw, IN (US); Daniel D. Auger, Ft. Wayne, IN (US)

(73) Assignee: DePuy Ireland Unlimited Company, Ringaskiddy (IE)

(*) Notice: Subject to any disclaimer, the term of this patent is extended or adjusted under 35 U.S.C. 154(b) by 140 days.

(21) Appl. No.: 16/154,981

(22) Filed: Oct. 9, 2018

(65) Prior Publication Data

US 2019/0038430 A1 Feb. 7, 2019

Related U.S. Application Data

(62) Division of application No. 13/629,886, filed on Sep. 28, 2012, now Pat. No. 10,092,421.

(51) Int. Cl.
*A61F 2/46* (2006.01)

(52) U.S. Cl.
CPC ........ *A61F 2/461* (2013.01); *F04C 2270/041* (2013.01)

(58) Field of Classification Search
CPC .......... A61F 2/46; A61F 8/4603; A61F 2/461; A61F 2002/4627; A61F 2002/4635; A61F 2002/4637; A61B 17/16; A61B 17/1604; A61B 17/1657; A61B 17/1675
See application file for complete search history.

(56) References Cited

U.S. PATENT DOCUMENTS

| | | | |
|---|---|---|---|
| 5,059,196 A * | 10/1991 | Coates | A61F 2/461 269/229 |
| 5,061,270 A * | 10/1991 | Aboczky | A61F 2/4609 606/91 |
| 5,062,852 A | 11/1991 | Dorr et al. | |
| D337,639 S | 7/1993 | Beckman | |

(Continued)

FOREIGN PATENT DOCUMENTS

| | | |
|---|---|---|
| DE | 10013331 A1 | 9/2001 |
| EP | 780090 A1 | 6/1997 |

(Continued)

OTHER PUBLICATIONS

United Kingdom Search Report, UK Application No. GB0911643.5, dated Aug. 20, 2009, 2 pages.

(Continued)

*Primary Examiner* — Jessica Weiss
(74) *Attorney, Agent, or Firm* — Barnes & Thornburg LLP

(57) ABSTRACT

A surgical instrument and method for an orthopaedic arthroplasty procedure is disclosed. The instrument includes a shaft having a first end, a second end, and a longitudinal axis extending through a center of the shaft between the first and second ends. The surgical instrument further includes a spine extending outwardly from the first end of the shaft in a direction perpendicular to the longitudinal axis, wherein the spine has a longitudinal extent that is parallel to the longitudinal axis. When the surgical instrument is in contact with a tibial implant component, the spine is adapted to be positioned within an intercondylar notch of a femoral component.

5 Claims, 12 Drawing Sheets

(56) References Cited

U.S. PATENT DOCUMENTS

| | | | |
|---|---|---|---|
| 5,417,693 A * | 5/1995 | Sowden | A61B 17/1659 269/234 |
| 5,571,111 A | 11/1996 | Aboczky | |
| 5,732,992 A * | 3/1998 | Mauldin | A61F 2/461 294/119.1 |
| 5,788,701 A * | 8/1998 | McCue | A61F 2/461 606/88 |
| 5,902,339 A | 5/1999 | Keller | |
| 6,258,095 B1 * | 7/2001 | Lombardo | A61B 17/154 606/87 |
| 6,520,966 B1 * | 2/2003 | Kohler | A61F 2/461 606/86 R |
| 6,663,636 B1 | 12/2003 | Lin | |
| 8,277,460 B2 | 10/2012 | McMillan et al. | |
| 8,398,650 B1 * | 3/2013 | Burgi | A61F 2/4609 606/99 |
| 8,597,302 B2 | 12/2013 | Beedall et al. | |
| 9,737,408 B2 * | 8/2017 | Leszko | A61F 2/389 |
| 10,092,421 B2 | 10/2018 | Edwards et al. | |
| 2003/0100907 A1 * | 5/2003 | Rosa | A61B 17/155 606/86 R |
| 2003/0109929 A1 | 6/2003 | Keller | |
| 2004/0243134 A1 * | 12/2004 | Walker | A61B 34/20 606/79 |
| 2006/0116769 A1 | 6/2006 | Marnay et al. | |
| 2008/0119941 A1 | 5/2008 | Seo et al. | |
| 2010/0168753 A1 * | 7/2010 | Edwards | C23F 1/14 606/88 |
| 2010/0331992 A1 * | 12/2010 | Podolsky | A61F 2/3609 623/22.15 |
| 2011/0301613 A1 * | 12/2011 | Green, II | A61B 17/92 606/99 |
| 2012/0123429 A1 * | 5/2012 | Beedall | A61F 2/461 606/99 |
| 2013/0006370 A1 * | 1/2013 | Wogoman | A61F 2/4684 623/20.16 |
| 2013/0006376 A1 * | 1/2013 | Wogoman | A61F 2/389 623/20.32 |
| 2014/0094812 A1 * | 4/2014 | Edwards | A61F 2/461 606/88 |
| 2014/0094821 A1 * | 4/2014 | Wagner | A61F 2/461 606/99 |
| 2014/0277541 A1 * | 9/2014 | Wyss | A61F 2/461 623/20.32 |
| 2016/0199198 A1 * | 7/2016 | Dietz | A61F 2/461 606/99 |

FOREIGN PATENT DOCUMENTS

| | | |
|---|---|---|
| WO | 9325164 A1 | 12/1993 |
| WO | 2011004140 A2 | 1/2011 |

OTHER PUBLICATIONS

International Search Report, International Application No. PCT/GB2010/001278, dated Feb. 21, 2011, 5 pages.

Sigma Fixed Reference Surgical Technique, DePuy Orthopaedics, Inc., 2010, 52 pages.

European Search Report for European Application No. 13186421.7-1654, dated Jan. 17, 2014, 8 pages.

* cited by examiner

SURGICAL INSTRUMENT AND METHOD OF USE

This divisional application claims priority under 35 U.S.C. § 121 to U.S. patent application Ser. No. 13/629,886, now U.S. Pat. No. 10,092,421, which is expressly incorporated herein by reference.

TECHNICAL FIELD

The present disclosure relates to surgical instruments and, more particularly, to methods and apparatuses for stabilizing surgical instruments during use.

BACKGROUND

Joint arthroplasty is a well-known surgical procedure by which a diseased and/or damaged natural joint is replaced by a prosthetic joint. A typical knee prosthesis includes a tibial component and a femoral component adapted to contact a bearing surface of the tibial component. The tibial component typically includes a stem extending distally therefrom that is implanted in a prepared medullary canal of the patient's tibia.

To facilitate the replacement of the natural joint with the knee prosthesis, orthopaedic surgeons use a variety of orthopaedic surgical instruments such as, for example, trial components, drill guides, reamers, impactors, and other surgical instruments.

SUMMARY

According to an illustrative embodiment, a surgical instrument for use in an orthopaedic arthroplasty procedure comprises a shaft having a first end, a second end, and a longitudinal axis extending through a center of the shaft between the first and second ends. The surgical instrument further includes a spine extending outwardly from the first end of the shaft in a direction perpendicular to the longitudinal axis, wherein the spine has a longitudinal extent that is parallel to the longitudinal axis. When the surgical instrument is in contact with a tibial implant component, the spine is adapted to be positioned within an intercondylar notch of a femoral component.

In another illustrative embodiment, the spine extends outwardly from a first side of an impactor head that is removably attached to the first end of the shaft.

In a further illustrative embodiment, a gap is formed between the spine and walls forming the intercondylar notch that, in some tibial and femoral components, is small enough that the spine prevents rotational movement of the impactor head about a longitudinal axis of a tibia in which the tibial component is implanted and, in other tibial and femoral components, is large enough that the spine does not prevent rotation movement of the impactor head about the tibial longitudinal axis.

In still another illustrative embodiment, a cavity is disposed in a second side of the impactor head opposite the first side and the cavity is adapted to accommodate a tibial spine extending outwardly from the tibial implant component.

In an illustrative embodiment, a gap is formed between the tibial spine and walls forming the cavity that, in some tibial and femoral components, is small enough that the tibial spine prevents rotational movement of the impactor head about the tibial longitudinal axis and, in other tibial and femoral components, is large enough that the tibial spine does not prevent rotation movement of the impactor head about the longitudinal axis.

In a further illustrative embodiment, the gap between the spine and the walls forming the intercondylar notch is small and the gap between the tibial spine and the walls forming the cavity is large such that the spine prevents rotation of the impactor head.

In another illustrative embodiment, the gap between the spine and the walls forming the intercondylar notch is large and the gap between the tibial spine and the walls forming the cavity is small such that the tibial spine prevents rotation of the impactor head.

In an illustrative embodiment, the spine is non-removably attached to the first end of the shaft.

In yet another illustrative embodiment, the first end of the shaft further includes a connector adapted to be selectively attached to a plurality of different end pieces.

In a further illustrative embodiment, the surgical instrument includes an adapter for attachment to the spine, wherein the adapter may be selectively attached to the spine for use with larger femoral implant components.

In an illustrative embodiment, the femoral component is a femoral implant component.

In a further illustrative embodiment, an impactor for use in securing a tibial orthopaedic implant component within a bone surface comprises a shaft having a first end adapted to be impacted by a tool and an end piece having a first end and a second end. The first end of the end piece is connected to the second end of the shaft and a second end of the end piece includes an impaction surface, a first anti-rotation feature disposed in a first surface of the end piece, and a second anti-rotation feature disposed in a second surface of the end piece that is opposite the first surface. The first and second anti-rotation features are adapted for cooperation with the tibial implant component and a femoral component such that at least one of the first and second anti-rotation features orients the end piece when the impaction surface is in contact with the tibial implant component.

In yet another illustrative embodiment, the first anti-rotation feature is in the form of a spine disposed in a first side of the end piece and which is adapted for insertion within an intercondylar notch of the femoral component.

In another illustrative embodiment, a gap is formed between the spine and walls forming the intercondylar notch that, in some tibial and femoral components, is small enough that the spine prevents rotational movement of the impactor end piece about a longitudinal axis of a tibia in which the tibial implant component is implanted and, in other tibial and femoral components, is large enough that the spine does not prevent rotation movement of the end piece about the tibial longitudinal axis.

In a further illustrative embodiment, the second anti-rotation feature is in the form of a cavity disposed in a second side of the impactor head opposite the first side and the cavity is adapted to accommodate a tibial spine extending outwardly from the tibial implant component.

In an illustrative embodiment, a gap is formed between the tibial spine and walls forming the cavity that, in some tibial and femoral components, is small enough that the tibial spine prevents rotational movement of the impactor head about the tibial longitudinal axis and, in other tibial and femoral components, is large enough that the tibial spine does not prevent rotation movement of the impactor head about the tibial longitudinal axis.

In another illustrative embodiment, the femoral component is a femoral implant component.

In still another illustrative embodiment, a method of using a surgical instrument during an orthopaedic arthroplasty procedure is disclosed, wherein the surgical instrument includes a shaft including a first end and a second end and a spine extending outwardly from the first end of the shaft. The method includes the steps of flexing a knee of a patient and inserting a tibial implant component within a resected/prepared tibia of the patient. The method further includes the step of positioning an end of the surgical instrument in contact with a tibial implant component with the spine positioned to orient and prevent rotation of the surgical instrument.

In a further illustrative embodiment, the method includes the step of securing a femoral implant component to a resected femur of the patient after the positioning step.

In another illustrative embodiment, the method includes the step of securing a femoral implant component to a resected femur of the patient prior to the positioning step.

In an illustrative embodiment, the spine extends from a first side of the surgical instrument and a cavity is disposed within a second side of the surgical instrument opposite the first side and wherein the method further includes the step of positioning the end of the surgical instrument with a tibial spine of the tibial implant component extending into the cavity.

In yet another illustrative embodiment, the method includes the step of orienting and preventing rotation of the surgical instrument by the spine or the cavity of the surgical instrument depending on a size of the tibial and femoral implant components.

In a further illustrative embodiment, the positioning step includes positioning the surgical instrument with the spine extending into an intercondylar notch of the femoral component.

In another illustrative embodiment, the spine has a width greater than a width of an intercondylar notch of the femoral component and the positioning step includes positioning the surgical instrument with the spine spaced from condyles of the femoral component to orient and prevent rotation of the surgical instrument.

Other aspects and advantages of the present disclosure will become apparent upon consideration of the following drawings and detailed description, wherein similar structures have similar reference numbers.

BRIEF DESCRIPTION OF THE DRAWINGS

The detailed description particularly refers to the following figures, in which.

DETAILED DESCRIPTION OF THE DRAWINGS

Figure 1:
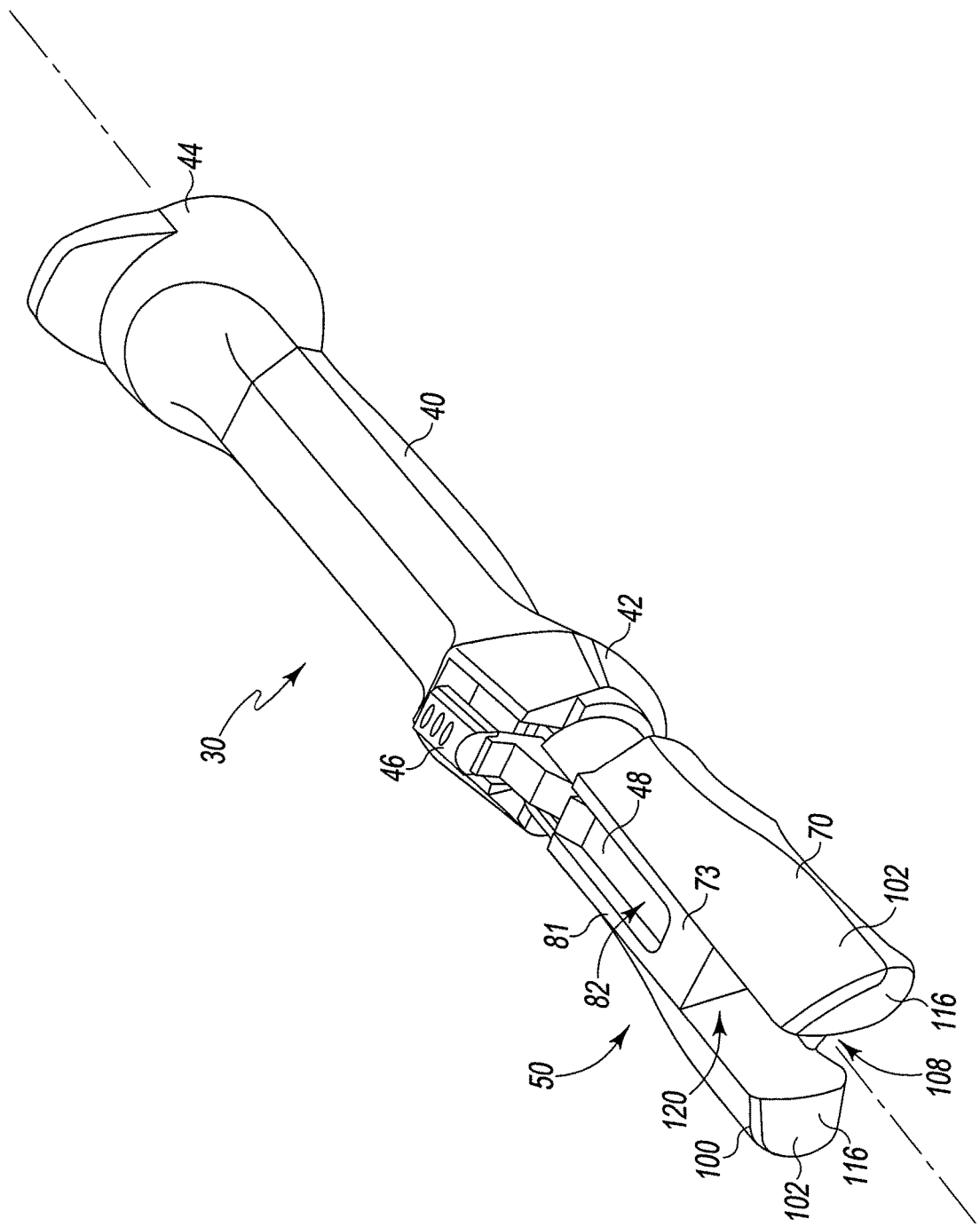
FIG. 1 is a perspective view of an impactor head attached to an end of a tool, wherein the impactor head is used to aid in driving a tibial implant component into a tibia of a patient.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-4, a first embodiment of a tool 30 for driving an implant component (as shown in FIGS. 5-9) into a tibial bone surface 34 is shown. The implant component is in the form of a tibial component 36 forming a portion of a posterior stabilized knee orthopaedic prosthesis in combination with a femoral component 37.

The tibial component 36 is illustratively formed from a polymeric material such as ultra-high molecular weight polyethylene (UHMWPE), but may be formed from other materials, such as a ceramic material, a metallic material, a bio-engineered material, or the like. The tibial component 36 is configured to be secured to the tibial bone surface 34 in the form of a surgically-prepared proximal end of a patient's tibia. The femoral component 37 is illustratively formed of a metallic material, but may be formed of other suitable materials. The femoral component 37 is configured to articulate with the tibial component 36.

Figure 2:
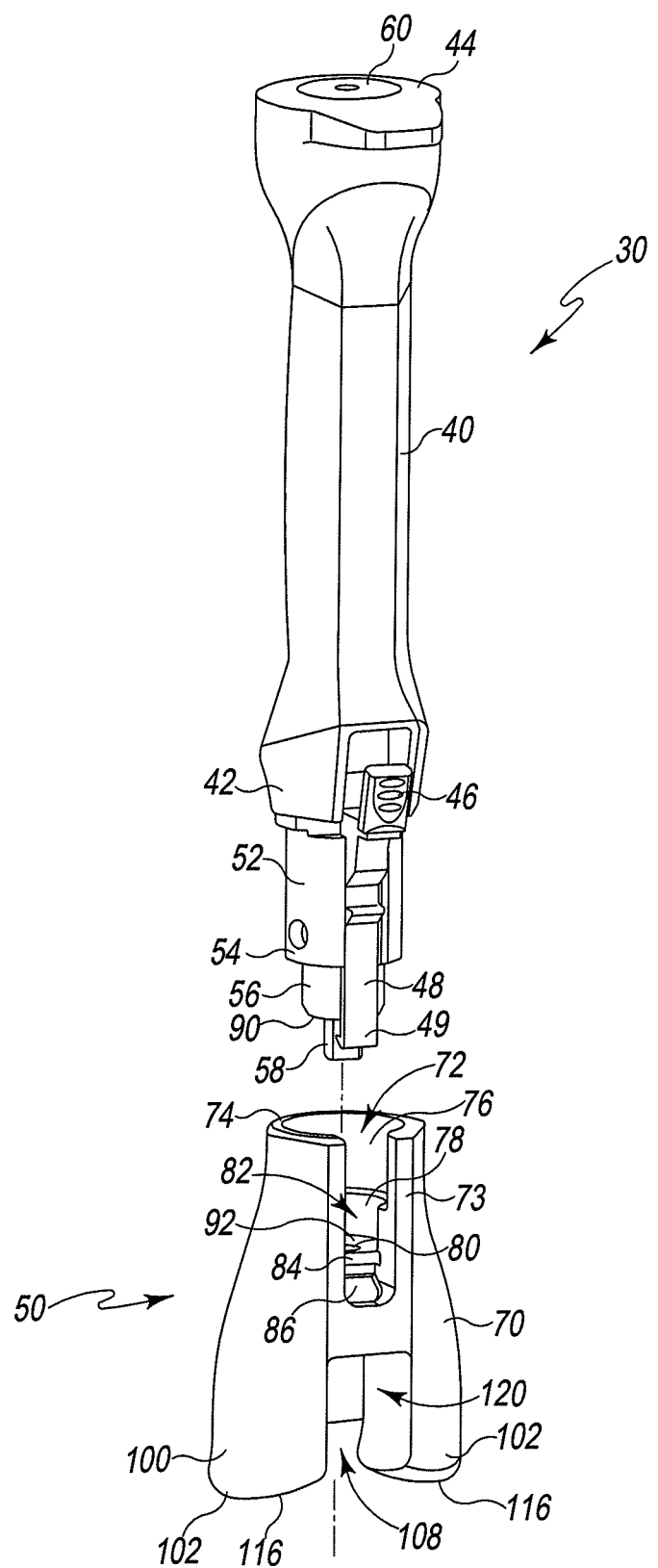
FIG. 2 is an exploded perspective view of the tool and the impactor head of FIG. 1.

As best seen in FIGS. 1 and 2, the tool 30 includes a central shaft 40 having an attachment end 42 and a free end 44. The attachment end 42 includes a universal quick-release connector having a lever arm 46 that operates a latch finger 48. A latch 49 is disposed at an end of the latch finger 48 to easily attach and detach various instrument end pieces to the tool 30, for example, an impactor head 50. The latch finger 48 is biased to a closed position such that inward movement of the lever arm 46 opens the latch 48. The attachment end 42 further includes a central projection 52 formed of a plurality of concentric cylinders 54, 56, 58 each extending from the next and each having a smaller diameter than the cylinder 54, 56, 58 from which it extends, with the cylinder 58 having a smallest diameter and the cylinder 54 having a largest diameter.

While the tool 30 is described herein as having an impactor head 50 attached thereto, any instrument end piece may be connected to the universal connector of the tool 30 including, but not limited to, punches, reamers, inserters, extractors, impactors, or any other instruments in which use of a hand piece or tool for controlling the instrument end piece is desired. During a particular surgery, the tool 30 may be utilized with a plurality of different end pieces to minimize the number of tools necessary in an operating room.

The free end 44 of the tool 30 has a generally rounded form with a central, slightly raised circular portion 60, as seen in FIG. 2, that provides a strike zone for receiving a blow from a tool, such as a hammer or mallet, during use of the tool 30. The central shaft 40 forms a handle by which the tool 30 may be grasped during use.

Figure 3:
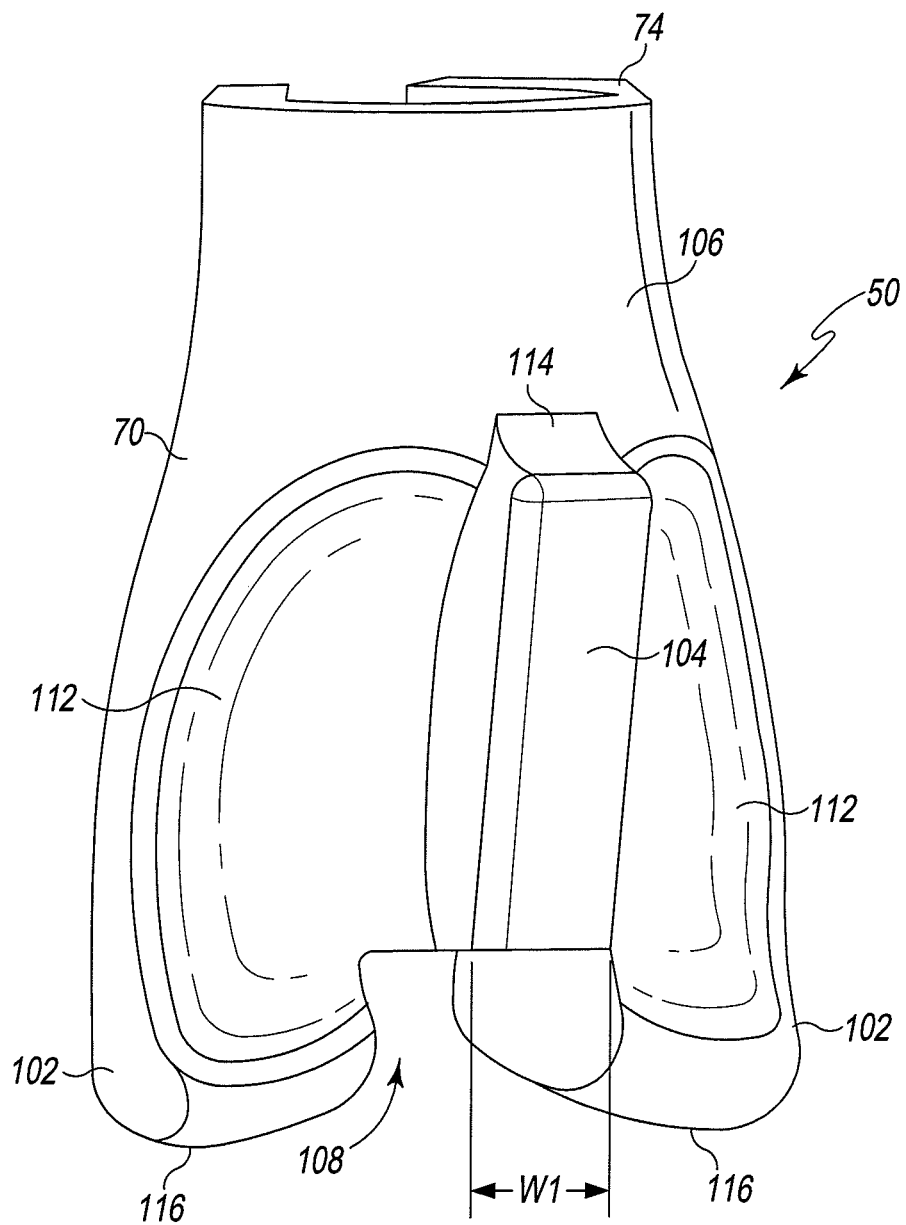
FIG. 3 is a perspective view of a rear side of the impactor head of FIGS. 1 and 2 and showing an anti-rotation feature in the form of a spine.
Figure 4:
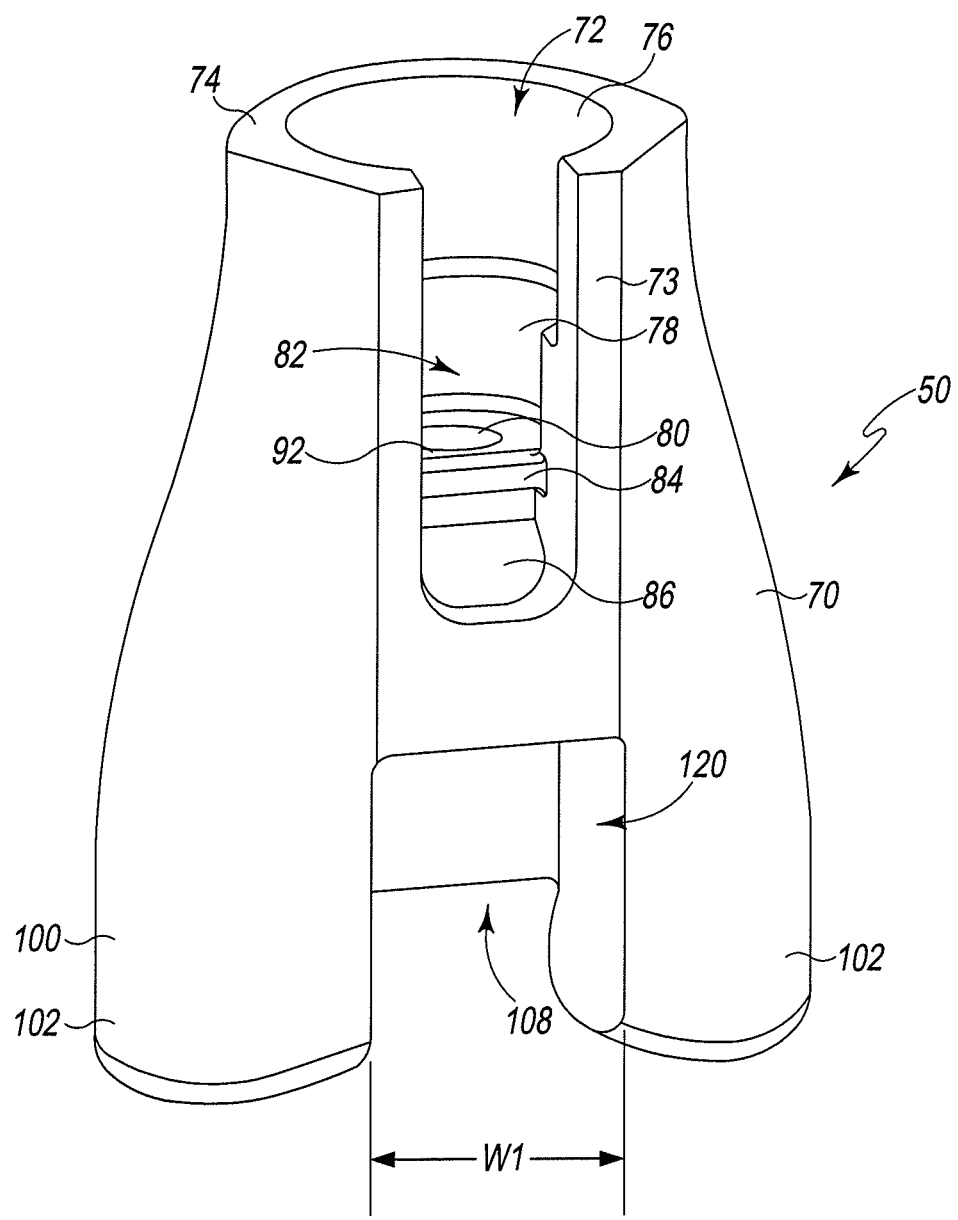
FIG. 4 is a perspective view of a front side of the impactor head of FIGS. 1 and 2 and depicting an anti-rotation feature in the form of a cavity.

Referring to FIGS. 3 and 4, the impactor head 50 includes a body 70 having a cavity 72 formed in a front surface 73 of an attachment end 74 of the impactor head 50. The cavity 72 includes cylindrical walls 76, 78, 80 that are concentrically disposed with respect to one another and stepped in diameter to form corresponding cylindrical cavities. In particular, the wall 76 has a diameter greater than diameters of the walls 78, 80 and the wall 78 has a diameter greater than the diameter of the wall 80. The walls 76, 78, 80 are sized to accommodate the cylinders 54, 56, 58, respectively, of the central projection 52 extending from the attachment end 42 of the tool 30, as will be discussed in greater detail below.

As seen in FIG. 4, the impactor head 50 further includes an outer wall 81 having a cutout 82 formed therein, wherein the cutout 82 is in partial communication with the cavity 72 and extends below the cavity 72. A protrusion 84 extends outwardly from a surface 86 formed in the cutout 82 and is spaced inwardly of the outer wall 81.

The impactor head 50 is illustratively formed from a polymeric material such as ultra-high molecular weight polyethylene (UHMWPE), polyetheretherketone (PEEK), polyphenylsulfone (PPSU), polycarbonate (PC), but may be formed from other suitable materials.

The impactor head 50 is attached to the tool 30 by depressing the lever arm 46, thereby rotating the latch finger 48 about a hinge and lifting the latch finger 48. During this operation, the tool 30 is rotated until the latch finger 48 is aligned with the cutout 82 in the outer wall 80 of the impactor head 50 and the projection 52 of the tool 30 is inserted into the cavity 72 of the impactor head 50 with the cylinders 54, 56, 58 adjacent the walls 76, 78, 80, respectively. The projection 52 is inserted until an outer surface 90 of the cylinder 56 is adjacent an inner surface 92 forming a cylindrical cavity with the cylindrical wall 78. The lever arm 46 is thereafter released such that the latch finger 48 enters the cutout 82 and the latch 49 interferes with the protrusion 84 to prevent removal of the impactor head 50 from the tool 30. In a similar manner, the impactor head 50 may be removed by depressing the lever arm 46, thereby moving the latch finger 48 out of the cutout 82 and, thus, moving the latch 49 out of interference with the protrusion 84.

As discussed above, other instrument end pieces may be utilized with the tool 30. The other instrument end pieces may include structures similar to those of the impactor head 50, for example the cylindrical walls 76, 78, 80, the cutout 82, and the protrusion 84, to accommodate the attachment structures of the tool 30.

Referring to FIGS. 3 and 4, an impact end 100 of the impactor head 50 opposite the attachment end 74 includes a two spaced-apart impaction legs 102. A spine 104 extends outwardly from a rear surface 106 of the impactor head 50 and has a width W1. The spine 104 ends at a gap 108 formed in the rear surface 106 of the impactor head 50 between the impaction legs 102. Concave surfaces 112 are formed within the rear surface 106 of the impactor head 50 in each of the legs 102, wherein the concave surfaces 112 extend between an upper edge 114 of the spine 104 and impaction surfaces 116 of the impaction legs 102. A cavity 110 is formed in the front surface 73 of the impactor head 50 and has a width W2 extending laterally between the impaction legs 102. The cavity 110 extends longitudinally between the impaction surfaces 116 and a point spaced from the cutout 82.

Figure 5:
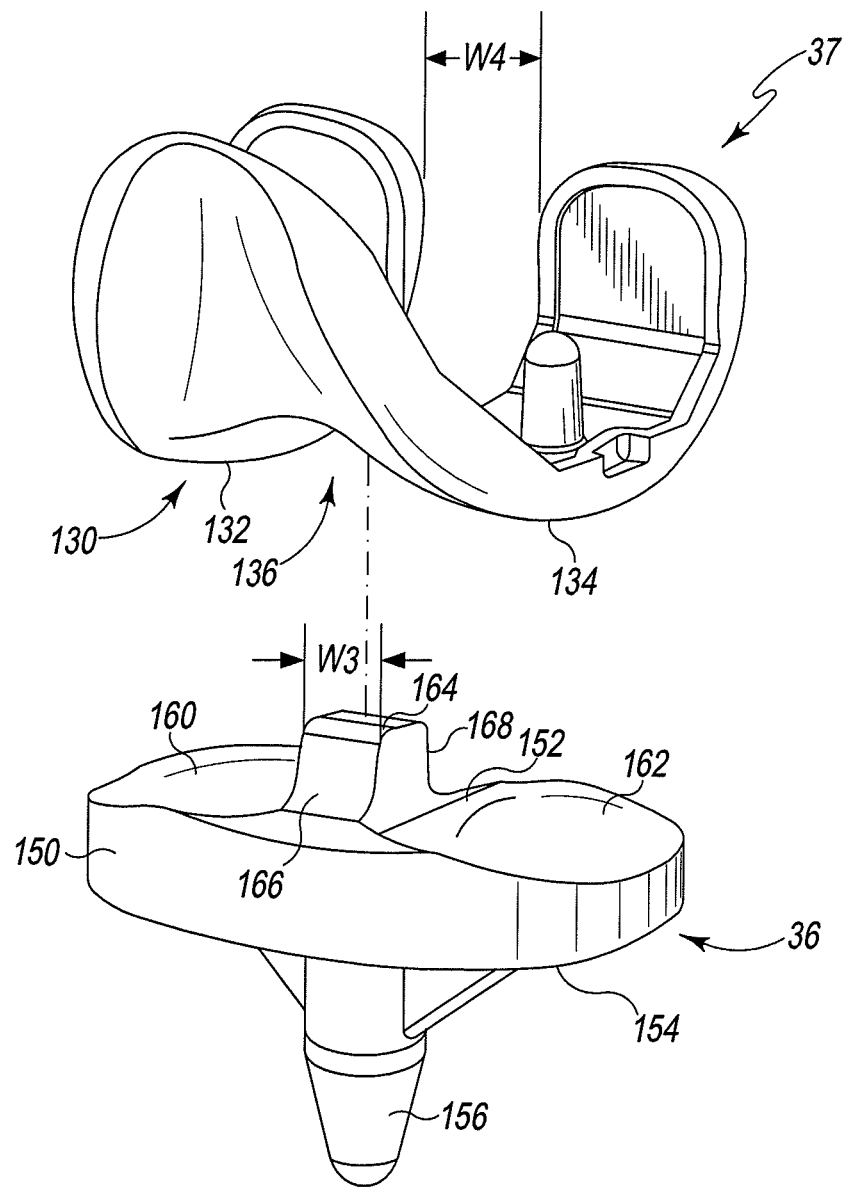
FIG. 5 is an exploded perspective view of a fixed bearing tibial implant component and a femoral implant component.

Referring to FIG. 5, the femoral component 37 is configured to be coupled to a surgically-prepared surface of a distal end of a patient's femur (not shown). The femoral component 37 may be secured to the patient's femur using bone adhesive or any other suitable attachment means. The femoral component 37 includes an articulating surface 130 having a pair of spaced apart medial and lateral condyles 132, 134. In use, the condyles 132, 134 replace the natural condyles of the patient's femur. The condyles 132, 134 are spaced apart to define an intercondylar notch or recess 136 having a width W4 therebetween. While a particular femoral component 37 is depicted, the principles of the present application may be used with any femoral component.

The tibial component 36, as seen, for example, in FIG. 5, includes a platform 150 having an upper bearing surface 152 and a bottom surface 154. The tibial component 36 includes a stem 156 extending downwardly from the bottom surface 154 of the platform 150. The stem 156 is received into a bore 158 formed within the resected/prepared bone surface 34 of the tibia. The tibial component 36 is configured to be implanted within the bone surface 34, as will be discussed in detail below.

The upper bearing surface 152 of the tibial component 36 includes a medial bearing surface 160, a lateral bearing surface 162, and a spine 164 having a width W3 and extending upwardly from the platform 150. The medial and lateral bearing surfaces 160, 162 are configured to receive or otherwise contact the corresponding medial condyle 132 and lateral condyle 134 of the femoral component 37. The bearing surfaces 132, 134 may each have a concave contour, but may have other shapes or contours. The spine 164 is positioned between the bearing surfaces 160, 162 and includes an anterior side 166 and a posterior side 168. The spine 164 is configured to be received within the intercondylar notch 136 formed between the medial and lateral condyles 132, 134 of the femoral component 37. While a particular tibial component 36 is depicted, the principles of the present application may be used with other tibial components.

Although specific steps during the surgical procedure will be described in detail, one skilled in the art will appreciate that the present application is not limited to these specific steps and the tool 30 with the impactor head 50 attached may be used in any sequence of steps as preferred by a particular surgeon and depending on the steps necessary during the surgical procedure.

Use of the tool 30 with the attached impactor head 50 during a total knee replacement surgical procedure will now be briefly discussed with reference to FIGS. 6-9. After resection, reaming, and preparing of the tibia and femur, drilling of the proper holes in the patient's tibial bone surface 34 and a femoral bone surface (not shown), and appropriate sizing of the tibial and femoral components using trial components, the tool 30 and the impactor head 50 are used to secure the tibial component 36 to the patient's resected tibia 34. Bone cement may be used to help secure the tibial component 36 in place.

The impactor head 50 is attached to the tool 30 and the combination is used to secure the tibial component 36 within the resected tibia 34. In particular, once the tibial component 36 is positioned appropriately within the resected tibia 34, the impactor head 50 is placed in contact with the tibial component 36. Specifically, the impaction surfaces 116 are positioned against the medial and lateral bearing surfaces 160, 162 of the tibial component 36 with the medial and lateral condyles 132, 134 disposed within the concave surfaces 112 of the impactor head 50. In this position, the spine 164 extending from the tibial component 36 is positioned within the cavity 110 formed in the front surface 73 of the impactor head 50. In addition, the spine 104 of the impactor head 50 is positioned within the intercondylar notch 136 of the femoral component 37.

After the impactor head 50 is positioned appropriately against the tibial component 36, the tibial component 36 is driven into the resected tibia 34 by using a hammer, mallet, or other suitable tool to strike the free end 44 of the tool 30. The pressure exerted by striking the free end 44 of the tool 30 drives the tibial component 36 into the bore 158 formed within the resected bone surface 34 of the tibia until the bottom surface 154 of the tibial component 36 is correctly seated against an upper resected surface 34 of the tibia. A surgeon may need to strike the free end 44 of the tool 30 multiple times to appropriately seat the tibial component 36.

The femoral component 37 may be secured to a prepared femur either before or after securing the tibial component 36 to the tibia. If the femoral component 37 is secured after the tibial component 36, a natural intercondylar notch of a distal end of the femur would cooperate with the spine 104 to provide the proper stabilization.

Various sizes of tibial and femoral components 36, 37 may be provided. A single size of tibial and femoral implant components 36, 37 is selected for a patient, but rotation of the impactor head 50 is prevented regardless of the size of the tibial and femoral components 36, 37. In an illustrative embodiment, the tibial and femoral components 36, 37 may be provided in sizes 1-10 with size 1 being the smallest and size 10 being the largest. As the size of the tibial and femoral components 36, 37 increases, so may the features of the tibial and femoral components 36, 37, for example, the spine 164 of the tibial component 36 and the intercondylar notch 136 of the femoral component 37.

Figure 6:
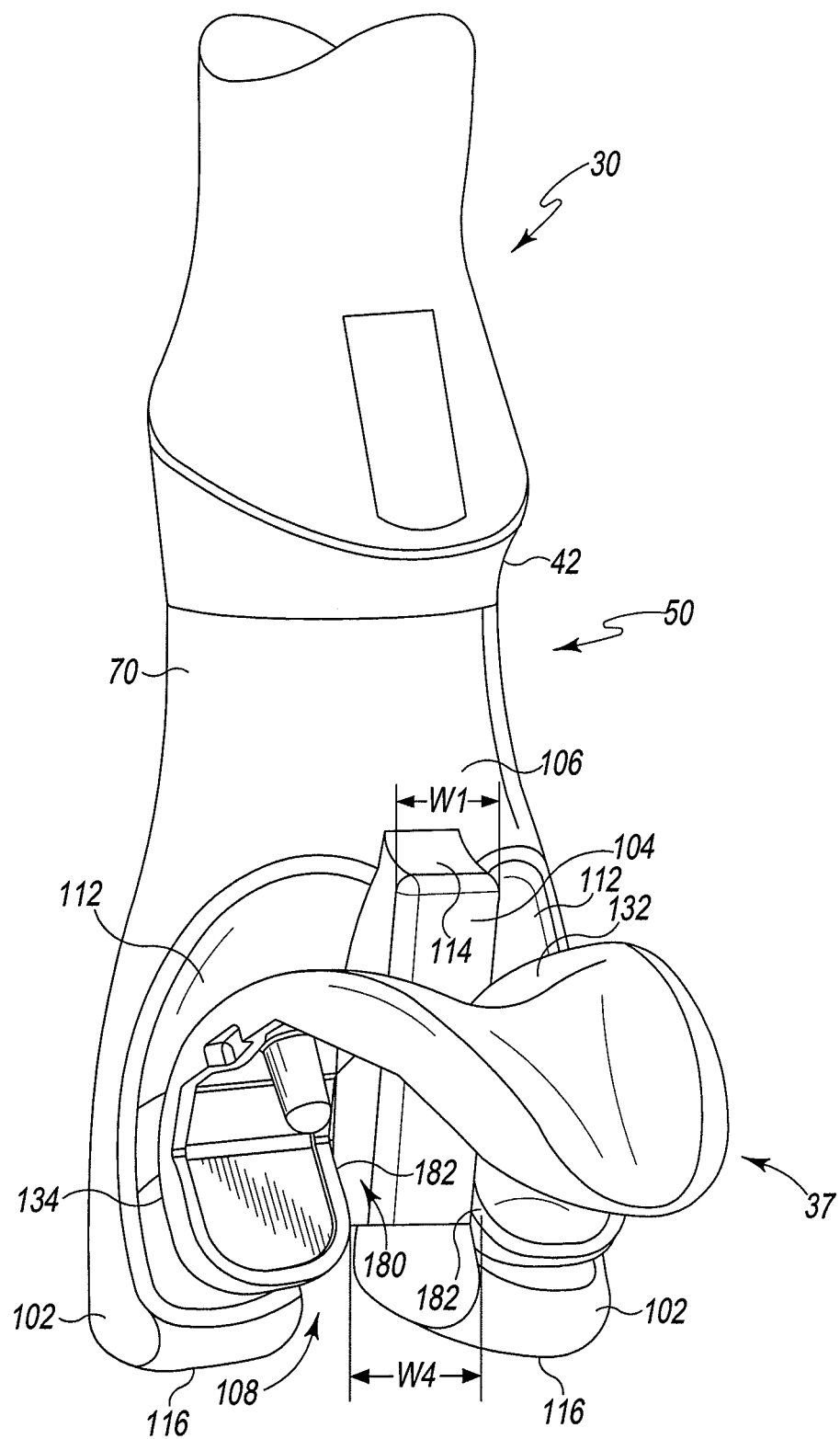
FIG. 6 is a rear perspective view of tibial and femoral implant components of a small size and depicting the femoral implant component at a 90 degree flexion angle.

If, for example, tibial and femoral components 36, 37 of sizes 1-5 are utilized, the width W1 of the spine 104 extending from the impactor head 50 and the width W4 of the intercondylar notch 136 are sized so as to create a small or no gap 180 between the spine 104 and walls 182 forming the intercondylar notch 136, as seen for example in FIG. 6. When the impactor head 50 is in contact with the tibial component 36, the spine 104 extends into the intercondylar notch 136, and the gap 180 prevents rotational movement of the impactor head 50 and the tool 30 about a longitudinal axis 185 of the tibia. The fit between the spine 104 and the intercondylar notch 136 also orients the tool 30 and the impactor head 50 about the longitudinal axis 185 of the tibia. Specifically, the intercondylar notch 136 orients the impactor head 50 in the proper position about the axis 185 on the tibial implant component 36. The cavity 110 of the impactor head 50 and the spine 164 of the tibial implant component 36 may also aid in this orientation.

Figure 7:
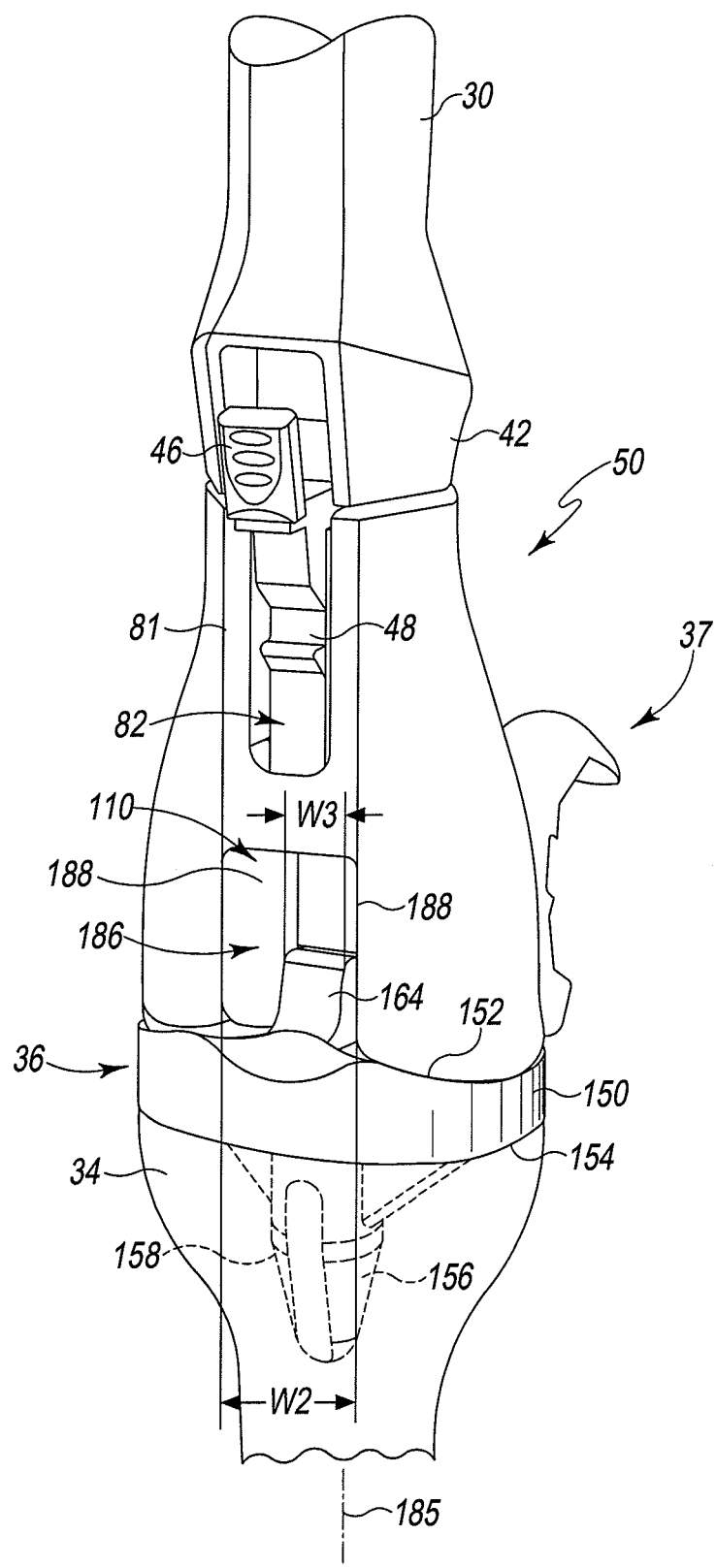
FIG. 7 is a front perspective view of the tibial and femoral implant components of FIG. 6.

Referring to FIG. 7, the width W3 of the spine 164 of the tibial component 37 and the width W2 of the cavity 110 of the impactor head 50 are sized so as to create a large gap 186 between the spine 164 and walls 188 forming the cavity 110. The walls 188 forming the cavity 110 therefore provide no rotational stability to the impactor head 50 and the tool 30.

Figure 8:
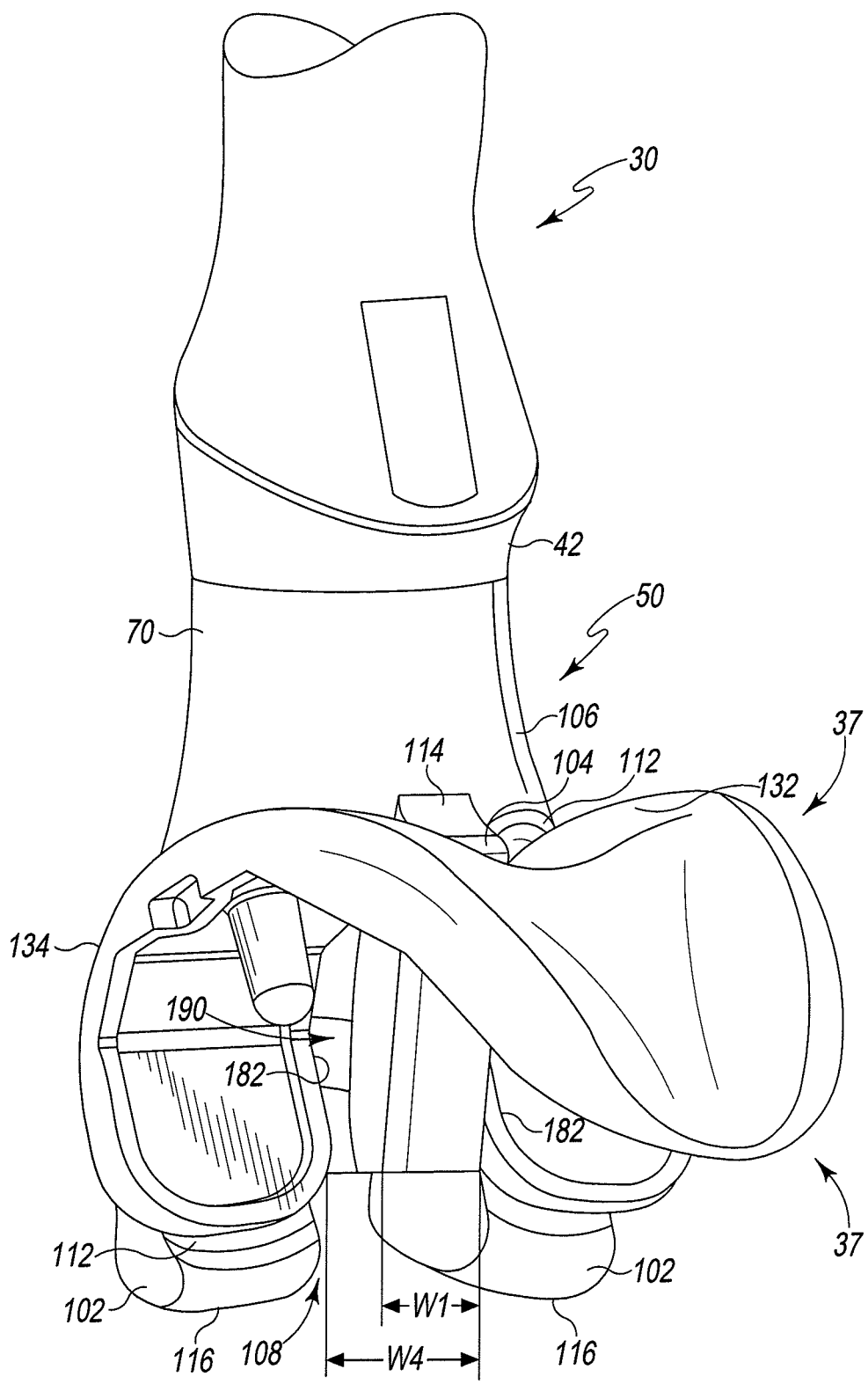
FIG. 8 is a rear perspective view of the tibial and femoral implant components of a large size and depicting the femoral implant at a 90 degree flexion angle.

If, for example, tibial and femoral components 36, 37 of sizes 6-10 are utilized, the width W1 of the spine 104 extending from the impactor head 50 and the width W4 of the intercondylar notch 136 are sized so as to create a large gap 190 between the spine 104 and the walls 182 forming the intercondylar notch 136, as seen in FIG. 8. When the impactor head 50 is in contact with the tibial component 36, the spine 104 extends into the intercondylar notch 136, but the large gap 190 therebetween provides no rotational stability to the impactor head 50 and the tool 30.

Figure 9:
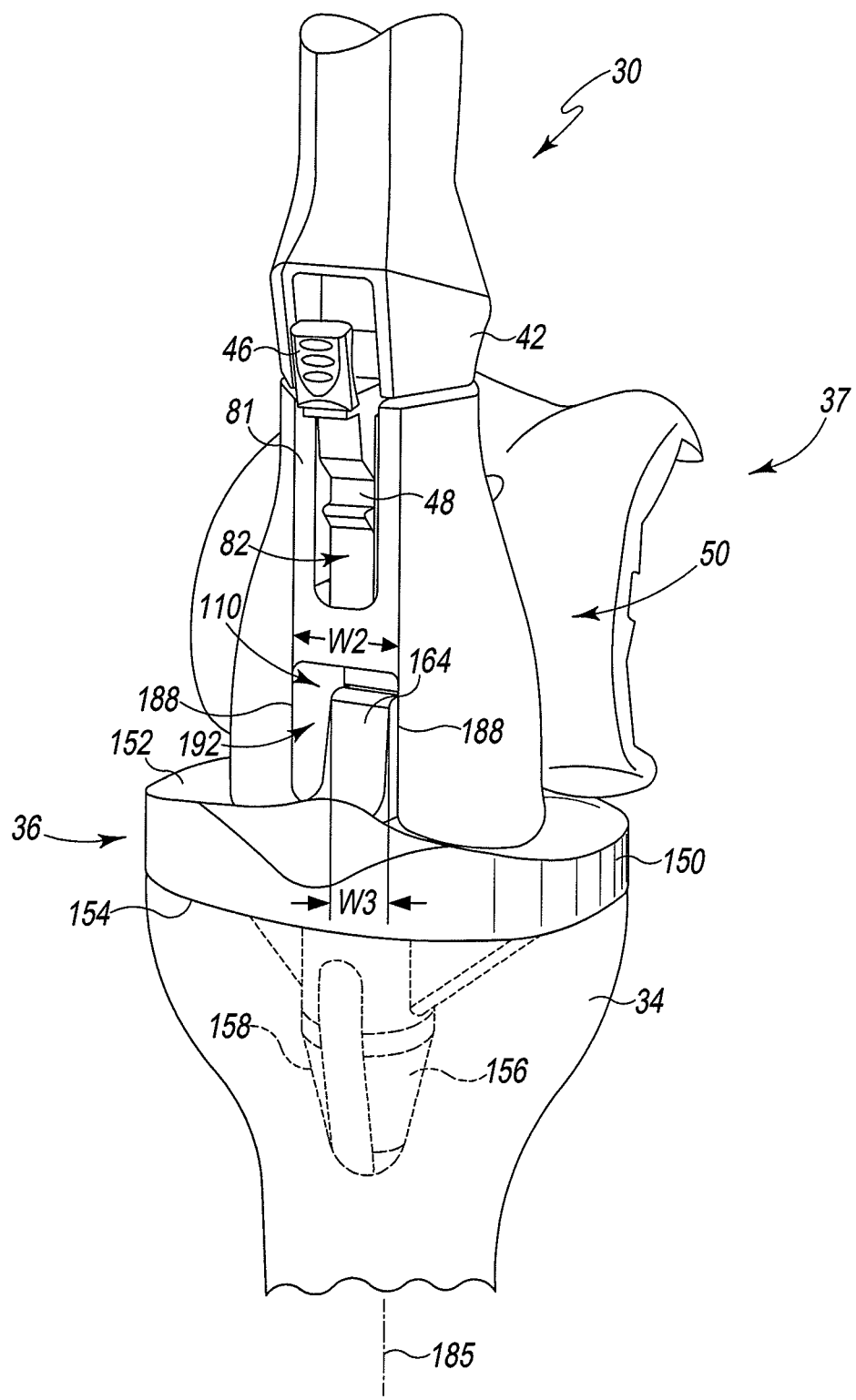
FIG. 9 is a front perspective view of the tibial and femoral implant components of FIG. 8.

As seen in FIG. 9, the width W3 of the spine 164 of the tibial component 37 and the width W2 of the cavity 110 of the impactor head 50 are sized so as to create a small or no gap 192 between the spine 164 and the walls 188 forming the cavity 110. The snug fit between the walls 188 and the spine 164 therefore prevents rotational movement of the impactor head 50 and the tool 30. The fit between the spine 164 and the cavity 110 orients the tool 30 and the impactor head 50. In particular, the cavity 110 orients the impactor head 50 in the proper position about the axis 185 on the tibial implant component 36. The spine 104 on the impactor head 50 and the intercondylar notch 136 may also aid in this orientation.

The impactor head 50 with two anti-rotation and orienting features, namely the spine 104 and the cavity 110 of the impactor head 50 that cooperate with the femoral component 37 and the tibial component 36, respectively, provides a single tool for use with a variety of differently-sized tibial and femoral implant components 36, 37. Previous designs would require a separate impactor head 50 for each size set of tibial and femoral implant components 36, 37.

The fit between the spine 104 of the impactor head 50 and the intercondylar notch 136 of the femoral component 37 or the fit between the cavity 110 and the spine 64 of the tibial component 36 prevent rotation of the impactor head 50 depending on a size of the tibial and femoral components 36, 37. This allows for proper alignment of the impactor head 50 adjacent the tibial and femoral components 36, 37 prior to and during use of the tool 30 and the impactor head 50. Forces transmitted by the tool 30 and the impactor head 50 will therefore be transmitted evenly and to the proper areas of the tibial component 36.

While a specific illustrative embodiment is disclosed herein, it should be understood that the impactor head 50 may be suitable for use with any number of different sizes of tibial and femoral components 36, 37. Still further, while the spine 104 is shown as being smaller to accommodate smaller femoral components 37 and the cavity 110 is shown as being larger to accommodate larger tibial components 36, the spine 104 may be larger to accommodate larger femoral components 37 and the cavity 110 could be smaller to accommodate smaller tibial components 36.

Figure 10:
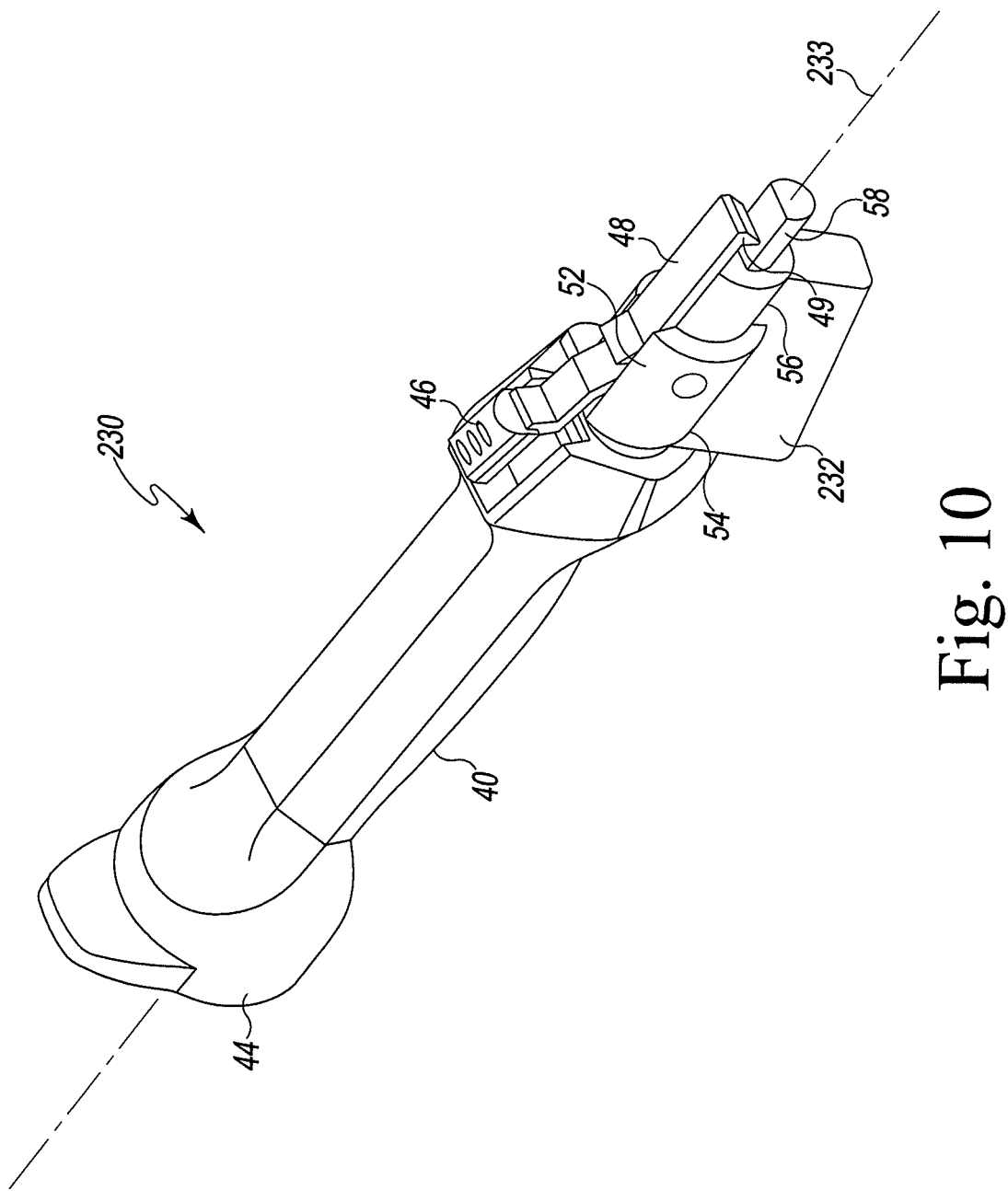
FIG. 10 is a perspective view of a tool to which a number of different instrument end pieces may be attached.
Figure 11:
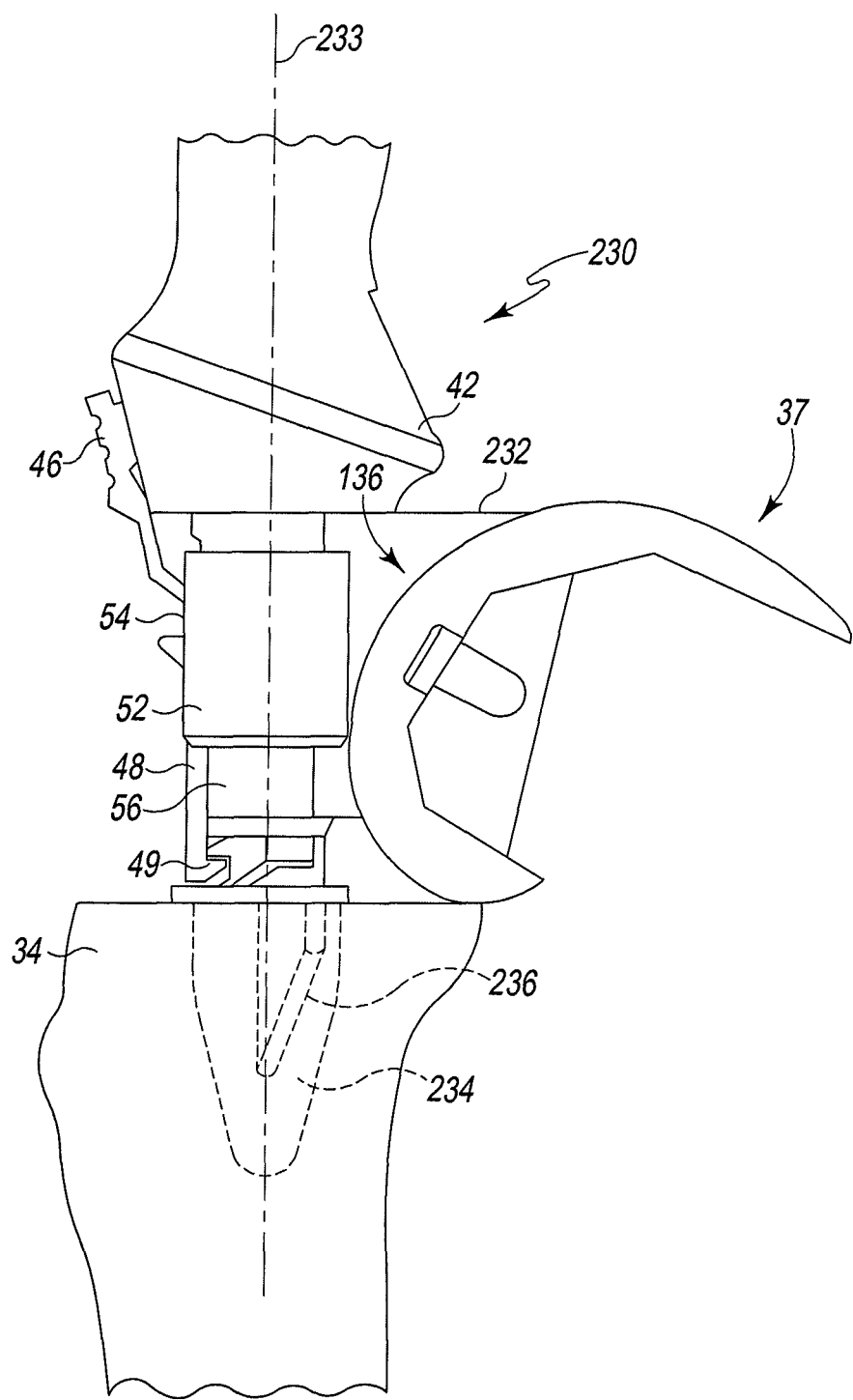
FIG. 11 is a side elevational view of the tool of FIG. 10 with a keel punch attached to an end of the tool and after the keel punch has been driven into a tibial bone surface of a patient.

A further tool 230 is depicted in FIGS. 10-11, wherein the tool 230 is similar to the tool 30 described in detail above. Rather than having an impactor head or other implement with a spine, the tool 230 includes a spine 232 extending outwardly from the central projection 52 opposite the lever arm 46. Alternatively, the spine 232 may be positioned at any location around a circumference of the central projection 52. The spine 232 is perpendicular to a longitudinal axis 190 of the tool 230 and has a longitudinal extent that is parallel to the longitudinal axis 190. Although the spine 232 is depicted as being integral with the central projection 52, the spine 232 could optionally be attached to the central projection 52. As can be seen in FIG. 11, any instrument end piece, for example a keel punch 234, may be attached to the tool 230 in the manner disclosed in detail above with respect to the tool 30.

The tool 230 with the keel punch 234 or other instrument end piece attached thereto may be utilized by aligning the spine 232 with the intercondylar notch 136 of the femoral component 37. Specifically, the keel punch 234 or other instrument end piece may include features, such as laterally extending anchors 236, that must be positioned in a particular orientation within the tibial bone surface 34. When attached to the tool 230 and aligned with the tibial bone surface 34, positioning of the spine 232 within the intercondylar notch 136 orients the tool 230 and the keel punch 234 in the proper orientation for being driven into the tibial bone surface 34 and further prevents rotation of the tool 230 and the keel punch 234.

Depending on the size of the femoral implant component 37, one or more differently-sized adapters may be attached to the spine 232 to add width to the spine 232. In this manner, the spine 232 may be used with a variety of differently-sized femoral implant components 37.

The tool 230 may be used in conjunction with various other instrument end pieces during the surgical process, for example, an impactor head for impacting and securing the tibial implant component 36 within the tibial bone surface 34. Regardless of what end piece is used, the spine 234 provides the same guidance with respect to orientation to the end piece and further prevents rotation of the end piece and the tool 230.

While particular tibial and femoral implant components are depicted herein, the principles of the present application may be used with other tibial and femoral implant components.

Figure 12:
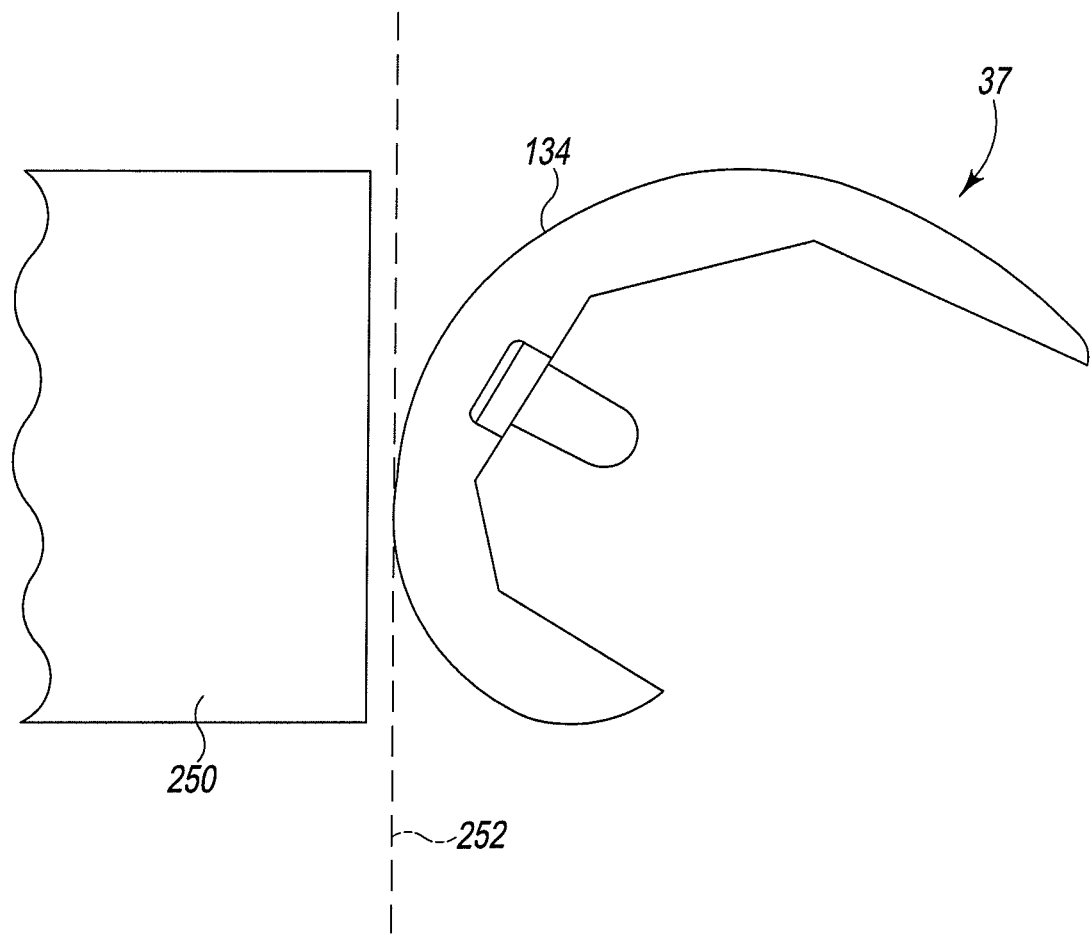
FIG. 12 is a side elevational view of a further embodiment of a further anti-rotation feature interfacing with bearing surfaces of a femoral implant component.

While spines or projections are disclosed herein as orienting and preventing rotation of an instrument and/or instrument end piece, the spine may be replaced by other suitable structures, for example, a spine 250, as seen in FIG. 12, that has a width greater than a width of the intercondylar notch 136 and that may abut or be spaced from the medial and lateral condyles 132, 134. In this embodiment, the spine 250 may orient and prevent rotation of the end piece in the same manner as the spines disclosed herein. Specifically, the spine 250 may be parallel to a plane 252 formed through distal ends of the medial and lateral condyles 132, 134. Any rotational movement of the spine 250 may be prevented by the condyles 132, 134.

As will become apparent from reading the present specification, any of the features of any of the embodiments disclosed herein may be incorporated within any of the other embodiments without departing from the scope of the present disclosure.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A method of using a surgical instrument during an orthopaedic arthroplasty procedure, the surgical instrument having a shaft and an impactor head with a spine extending outwardly therefrom, the method including the steps of:
    flexing a knee of a patient;
    inserting a tibial implant component within a prepared tibia of the patient; and
    positioning the impactor head of the surgical instrument in contact with the tibial implant component with the spine positioned to orient and prevent rotation of the surgical instrument with respect to the tibial implant component.

2. The method of claim 1, further including the step of securing a femoral implant component to a resected femur of the patient after the positioning step.

3. The method of claim 1, further including the step of securing a femoral implant component to a resected femur of the patient prior to the positioning step.

4. The method of claim 1, wherein the spine extends from a first side of the impactor head and wherein a cavity is disposed within a second side of the impactor head opposite the first side, the method further comprising the step of:
    positioning the impactor head of the surgical instrument such that a tibial spine of the tibial implant component extends into the cavity.

5. The method of claim 1, wherein the positioning step includes positioning the impactor head of the surgical instrument with the spine extending into an intercondylar notch of a femoral component.

* * * * *